United States Patent
Miyazawa et al.

(10) Patent No.: US 10,906,921 B2
(45) Date of Patent: Feb. 2, 2021

(54) BASE GENERATOR, REAGENT, ORGANIC SALT, COMPOSITION, METHOD FOR MANUFACTURING DEVICE, CURED FILM AND DEVICE

(71) Applicant: TOYO GOSEI CO., LTD., Chiba (JP)

(72) Inventors: Takashi Miyazawa, Chiba (JP); Yuki Toma, Chiba (JP)

(73) Assignee: TOYO GOSEI CO., LTD., Chiba (JP)

( * ) Notice: Subject to any disclaimer, the term of this patent is extended or adjusted under 35 U.S.C. 154(b) by 0 days.

(21) Appl. No.: 16/098,526

(22) PCT Filed: May 10, 2017

(86) PCT No.: PCT/JP2017/017680
§ 371 (c)(1),
(2) Date: Nov. 2, 2018

(87) PCT Pub. No.: WO2017/195822
PCT Pub. Date: Nov. 16, 2017

(65) Prior Publication Data
US 2019/0330247 A1    Oct. 31, 2019

(30) Foreign Application Priority Data

May 10, 2016 (JP) ................. 2016-094853

(51) Int. Cl.
| | | |
|---|---|---|
| C07F 7/02 | (2006.01) | |
| C07C 211/62 | (2006.01) | |
| C07F 9/547 | (2006.01) | |
| C08G 59/14 | (2006.01) | |
| G03F 7/004 | (2006.01) | |

(52) U.S. Cl.
CPC ............ *C07F 7/025* (2013.01); *C07C 211/62* (2013.01); *C07F 9/5475* (2013.01); *C08G 59/145* (2013.01); *G03F 7/0045* (2013.01)

(58) Field of Classification Search
CPC .... C07C 211/62; C07F 9/5475; C08G 59/145
USPC ........................................................ 549/214
See application file for complete search history.

(56) References Cited

U.S. PATENT DOCUMENTS

| 6,245,835 B1 | 6/2001 | Klein et al. |
| 2005/0075474 A1 | 4/2005 | Horimoto et al. |
| 2007/0010601 A1 | 1/2007 | Horimoto et al. |
| 2009/0023840 A1 | 1/2009 | Horimoto et al. |

FOREIGN PATENT DOCUMENTS

| JP | 51100196 | * | 9/1976 | |
| JP | 03116958 | * | 5/1991 | |
| JP | 2000-505497 A | | 5/2000 | |
| JP | 2005-298794 A | | 10/2005 | |
| JP | 2006-124643 A | | 5/2006 | |
| JP | 2006-348283 A | | 12/2006 | |
| JP | 2008-189824 A | | 8/2008 | |
| JP | 2013-136662 A | | 7/2013 | |
| JP | 2013-185147 A | | 9/2013 | |
| JP | 2014070035 | * | 4/2014 | |
| NL | 6504584 | * | 10/1965 | |
| WO | WO-2020054356 A1 | * | 3/2020 | ............. C08G 59/62 |

OTHER PUBLICATIONS

Vincent; Papers presented at the Meeting—American Chemical Society, Division of Organic Coatings and Plastics Chemistry, 1968, 28 (1), 504-511, 1968. Abstract from Chemical Abstracts CAPLUS Database; Accession No. 1969:525384, CAN 71:125384; with substance listing, 4 pages. (Year: 1968).*
Bindu; Phosphorus, Sulfur Silicon Relat. Elem. 2003, 178, 2373-2386. (Year: 2003).*
Necas; Czech Patent CS 183195, May 15, 1980. Abstract from Chemical Abstracts Caplus Database; Accession No. 1981: 193177, CAN 94:193177; with substance listing, 5 pages. (Year: 1980).*
International Search Report dated Jul. 4, 2017 of corresponding International Application No. PCT/JP2017/017680; 3 pgs.
Carre Francis et.al., Eine Verbindung mit hexakoordiniertern Silicium—ein Modell fuer den nucleophilen Angriff auf anionische, pentakoordinierte Siliciumspezies?, Angew.Chem. 101, 1989, No. 4, p. 474-476, 3 pgs.
Frnaziska Riedel et.al., A solvatochromic study of silicates and borate containing 4-nitrocatechol ligands, J.Phys.Org.Chem., 2008. Dec. 2003, 22, p. 203-211, 9 pgs.
Harrison Carole C. et.al., Novel Routes to Designer Silicas:Studies of the Decomposition of $(M+)2[Si(C6H4O2)3]$ . xH2O, J.Chem.Soc. Faraday Trans., 1995, 91(23), p. 4287-4297, 13 pgs.
Evans, Dennis F. et.al., Nuclear Magnetic Resonance Studies of Silicon(IV) Complexes in Aqueous Solution-I.Tris-Catecholato Complexes, Polyhedron, 1990, vol. 9,No. 6, p. 813-823, 13 pgs.
Cella, J.A. et.aL, 29Si NMR of Five- and Sixcoordinate Organosilicon Complexes, Journal of Organometallic Chemistry, 1980, 186, p. 13-17, 7 pgs.

* cited by examiner

*Primary Examiner* — Daniel R Carcanague
(74) *Attorney, Agent, or Firm* — Maier & Maier, PLLC

(57) ABSTRACT

A curing agent or a curing accelerator which is easy to synthesize and may cure an epoxy resin and the like, or may accelerate the curing is provided. A curing agent or a curing accelerator according to some embodiments of the present invention has a highly-coordinated silicon structure.

8 Claims, No Drawings

BASE GENERATOR, REAGENT, ORGANIC SALT, COMPOSITION, METHOD FOR MANUFACTURING DEVICE, CURED FILM AND DEVICE

TECHNICAL FIELD

Some of the embodiments of the present invention relate to a base generator, a curing agent, a curing accelerator, a reagent, an organic salt, a composition, a method for manufacturing a device, a cured film and a device.

BACKGROUND ART

One-pack epoxy resin composition is used for sealing and adhesion of various products such as electronic component and optical products. In the one-pack epoxy resin composition, a latent curing agent which does not react with an epoxy resin at room temperature and reacts only after being heated is used. As such latent curing agent, a so-called solid dispersed latent curing agent which is a powder having a high-melting point, being dispersed in the epoxy resin at room temperature and then melts and reacts upon heating is generally used. Among such, an amine-adduct type curing agent which is obtained by reacting an amine compound such as imidazole and the like with an epoxy compound is superior in the balance between curing characteristics and shelf stability (Patent Literature 1).

CITATION LIST

Patent Literature

[Patent Literature 1] JP 2000-505497B

SUMMARY OF INVENTION

Technical Problem

However, since the solid dispersed latent curing agent is generally a solid which does not dissolve in the epoxy resin, the solid dispersed latent curing agent hardly permeates into narrow gaps, and thus causes defective curing or non-uniform curing at the narrow gaps. Accordingly, its application has been limited.

Some of the embodiments of the present invention have been made in order to solve the afore-mentioned problems, and provide a curing agent or a curing accelerator which can be manufactured easily at low cost, and can cure a monomer and a resin such as epoxy resin.

Solution to Problem

A base generator according to some of the embodiments of the present invention includes: a negative ion; and a positive ion, wherein the negative ion has a first atom of group 14 element constituting a pentacoordinate structure or a hexacoordinate structure. When it is necessary to reduce the manufacturing cost of the base generator, the hexacoordinate structure of which starting material is relatively low in cost may be preferable. In addition, with the hexacoordinate structure, a plurality of base molecules can be generated from one structural unit. Accordingly, it may be superior in terms of base generating efficiency and curing characteristics.

The base generator, for example, includes either one of (1) to (3) below.

(1) A compound which generates a hydroxide ion by being dissolved in a solvent such as water, or a compound which directly generates a hydroxide ion.

(2) A compound which generates a chemical species or a substance which functions as a Broensted base receiving a proton.

(3) A compound which generates a Lewis base such as amine which may have a substituent group and an phosphine which may have a substituent group.

Regarding the base generator, the positive ion preferably has a second atom of group 15 element.

Regarding the base generator, the second atom is preferably a nitrogen atom or a phosphorus atom.

Regarding the base generator, it is preferable that the base is generated by decomposition of the positive ion. Typically, the base is generated by proton elimination and the like from the positive ion.

Regarding the base generator, it is preferable that the second atom has four bonds. For example, when the second atom is a nitrogen atom or a phosphorus atom, an amine or a phosphine having a strong nucleophilicity can be generated by cleaving one of the four bonds. Accordingly, the base generator can be an effective initiator for a monomer such as an epoxy compound and the like.

Regarding the base generator, it is preferable that the first atom is bonded to at least four third atoms of group 16 element.

Regarding the base generator, it is preferable that the third atom is an oxygen atom.

Regarding the base generator, it is preferable that the base is generated by heating the base generator to a temperature of 50° C. or higher.

Regarding the base generator, it is preferable that the base is generated by heating at a temperature of 110° C. or lower. For example, organic salts 18, 19, 21, 22 and 23 according to the embodiments of the present invention described later can cure a resin by one hour at the longest even when heated at a temperature of 80 to 110° C. or lower.

A reagent according to some embodiments of the present invention is a reagent which cures a monomer or a resin, or accelerates a curing of a monomer or a resin, comprising: a negative ion; and a positive ion, wherein the negative ion has a first atom of group 14 element constituting a pentacoordinate structure or a hexacoordinate structure.

Regarding the reagent, it is preferable that the positive ion has a second atom of group 15 element.

Regarding the reagent, it is preferable that in the negative ion, the first atom constitutes the hexacoordinate structure.

Regarding the reagent, it is preferable that a monomer or a resin is cured by heating to a temperature of 50° C. or higher. It is preferable that the base generator can generate a base by heating at a temperature of 110° C. or lower. For example, organic salts 18, 19, 21, 22 and 23 according to the embodiments of the present invention described later can cure a resin by one hour at the longest even under heating at a temperature of 80 to 110° C. or lower.

Regarding the reagent, it is preferable that the first atom is bonded to six oxygen atoms.

An organic salt according to some of the embodiments of the present invention is represented by the following general formula $$\begin{array}{c} Z^5 \diagdown \underset{Si}{\diagup} Z^1 \\ Z^4 \diagup \underset{Z^3}{\mid} \diagdown Z^2 \end{array} \quad \begin{array}{c} D \diagdown \underset{R^4}{\mid} \overset{+}{N} \diagup R^1 \\ R^3 \end{array} \qquad (1)$$

-continued

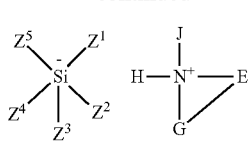

(2)

Here, [Each of $Z^1$ to $Z^5$ in the general formulas (3) and (4) represents: independently from each other, a hydrogen atom; a substituent group having a heteroatom of an atom of group 16 element such as an oxygen atom and a sulfur atom, an atom of group 15 element such as a nitrogen atom and a phosphorus atom, an atom of group 14 element other than a carbon atom such as a silicon atom or a halogen atom; or an organic group which may have a substituent group. In the case of the organic group, at least two of $Z^1$ to $Z^5$ may be bonded via at least one atom. Each of $R^1$ to $R^5$ in the general formulas (1) and (2) represents a substituent which may be the same or different from each other, and may have: a hydrogen atom; an atom of group 16 element such as an oxygen atom and a sulfur atom; an atom of group 15 element such as a nitrogen atom and a phosphorus atom; an atom of group 14 element other than a carbon atom such as a silicon atom; a heteroatom such as a halogen atom; or a substituent group. D in the general formulas (1) and (2) represents: an atom of group 16 element such as an oxygen atom and a sulfur atom; an atom of group 15 element such as a nitrogen atom and a phosphorus atom; an atom of group 14 element other than a carbon atom such as a silicon atom; a heteroatom such as a halogen atom; or an organic group which may have a substituent group. Each of E and G represents: independently from each other, an atom of group 16 element such as an oxygen atom and a sulfur atom; an atom of group 15 element such as a nitrogen atom and a phosphorus atom; an atom of group 14 element other than a carbon atom such as a silicon atom; a heteroatom such as a halogen atom; or an organic group which may have a substituent group. Each of H and J represents: independently from each other, a hydrogen atom; an atom of group 16 element such as an oxygen atom and a sulfur atom; an atom of group 15 element such as a nitrogen atom and a phosphorus atom; an atom of group 14 element other than a carbon atom such as a silicon atom; a heteroatom such as a halogen atom; or an organic group which may have a substituent group.]

Regarding the general formulas (1) and (2), it is preferable that each of the positive ion is a monovalent positive ion. When the positive ion is a monovalent positive ion, electrostatic interaction can be suppressed, allowing easier release from the electrostatic interaction, thereby resulting in easier generation of electrically neutral base.

An organic salt according to some of the embodiments of the present invention is represented by the following general formula (3) or (4).

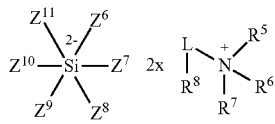

(3)

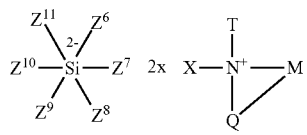

(4)

Here, [Each of $Z^6$ to $Z^{11}$ in the general formulas (3) and (4) represents: independently from each other, a hydrogen atom; a substituent group having a heteroatom of an atom of group 16 element such as an oxygen atom and a sulfur atom, an atom of group 15 element such as a nitrogen atom and a phosphorus atom, an atom of group 14 element other than a carbon atom such as a silicon atom or a halogen atom; or an organic group which may have a substituent group. In the case of the organic group, at least two of $Z^6$ to $Z^{11}$ may be bonded via at least one atom. Each of $R^5$ to $R^8$ in the general formulas (3) and (4) represents a substituent group which may be the same or different from each other, and may have: a hydrogen atom; an atom of group 16 element such as an oxygen atom and a sulfur atom; an atom of group 15 element such as a nitrogen atom and a phosphorus atom; an atom of group 14 element other than a carbon atom such as a silicon atom; a heteroatom such as a halogen atom; or a substituent group. L in the general formulas (3) and (4) represents: an atom of group 16 element such as an oxygen atom and a sulfur atom; an atom of group 15 element such as a nitrogen atom and a phosphorus atom; an atom of group 14 element other than a carbon atom such as a silicon atom; a heteroatom such as a halogen atom; or an organic group which may have a substituent group. Each of M and Q represents: independently from each other, an atom of group 16 element such as an oxygen atom and a sulfur atom; an atom of group 15 element such as a nitrogen atom and a phosphorus atom; an atom of group 14 element other than a carbon atom such as a silicon atom; a heteroatom such as a halogen atom; or an organic group which may have a substituent group. Each of T and X represents: independently from each other, a hydrogen atom; an atom of group 16 element such as an oxygen atom and a sulfur atom; an atom of group 15 element such as a nitrogen atom and a phosphorus atom; an atom of group 14 element other than a carbon atom such as a silicon atom; a heteroatom such as a halogen atom; or an organic group which may have a substituent group.]

Each of the general formulas (3) and (4) has two positive ions. Each of the positive ions is preferably a monovalent positive ion. When the positive ion is a monovalent positive ion, it is possible to generate a plurality of bases from the organic salt constituted by a negative ion and a plurality of positive ions, thereby improving curing characteristics.

Regarding the organic salt, it is preferable that D and L represent divalent organic group having a carbon atom. As a typical example of such organic salt, organic salt 1, 4, 13, 16 21 to 23 and the like described hereinafter can be mentioned. Example of a characteristic of such organic salt is that a heating temperature can be lowered when it is used as a reagent to accelerate polymerization of a substance such as an epoxy compound and the like by heating. Especially, benzylammonium-type organic salts such as organic salt 1, 4, 13, 16 21 to 23 and the like are superior in curing characteristics at low temperature, and can function as a curing agent and a curing accelerator at a temperature of 110° C. or lower, 80° C. for example. In addition, as in the case of organic salt 13, and 21 to 23, amount of amine generated from a unit structure can be improved by adopting hexacoordinate silicon anion as the counter anion, thereby curing efficiency improves.

Regarding the organic salt, it is preferable that $R^4$ and $R^8$ have an aromatic group.

Regarding the organic salt, it is preferable that E and G have a nitrogen atom. As the positive ion of the general formula (2), for example, an azolium cation which may have a substituent group and an imidazolium which may have a substituent group can be mentioned. Further, as a specific example of the azolium cation, 1,2,4-triazolium, oxazolium, oxadiazolium, thiadiazolium, benzotriazolium, hydroxybenzotriazolium, benzoxazolium, 1,2,3-benzothiadiazolium, 3-mercaptobenzotrizolium and the like can be mentioned. As the imidazolium cation, an unsubstituted imidazolium; an imidazolium having an organic group such as an alkyl group and an aryl group at its 2-position such as 2-methylimidazolium, 2-ethylimidazolium, 2-undecylimidazolium, 2-heptadecylimidazolium, 2-phenylimidazolium and the like; and an imidazolium having an organic group such as an alkyl group and an aryl group at another position in addition to the 2-position such as 2-ethyl-4-methylimidazolium, 1-benzyl-2-methylimidazolium, 1,2-dimethylimidazolium, 1-benzyl-2-phenylimidazolium, 1-benzyl-2-methylimidazole and 1-isobutyl-2-methylimidazolium can be mentioned. An imidazolium having a high polarity nitrile group such as 1-cyanoethyl-2-methylimidazolium, 1-cyanoethyl-2-undecylimidazolium, 1-cyanoethyl-2-ethyl-4-methylimidazolium, 1-cyanoethyl-2-phenylimidazolium and the like can be mentioned as an example.

Regarding the organic salt, it is preferable that M and Q have a nitrogen atom. As the positive ion of the general formula (4), for example, an azolium cation which may have a substituent group and an imidazolium which may have a substituent group can be mentioned. Further, as a specific example of the azolium cation, 1,2,4-triazolium, oxazolium, oxadiazolium, thiadiazolium, benzotriazolium, hydroxy benzotriazolium, benzoxazolium, 1,2,3-benzothiadiazolium, 3-mercaptobenzotrizolium and the like can be mentioned. As the imidazolium cation, an unsubstituted imidazolium; an imidazolium having an organic group such as an alkyl group and an aryl group at its 2-position such as 2-methylimidazolium, 2-ethylimidazolium, 2-undecylimidazolium, 2-heptadecylimidazolium, 2-phenylimidazolium and the like; and an imidazolium having an organic group such as an alkyl group and an aryl group at another position in addition to the 2-position such as 2-ethyl-4-methylimidazolium, 1-benzyl-2-methylimidazolium, 1,2-dimethylimidazolium, 1-benzyl-2-phenylimidazolium, 1-benzyl-2-methylimidazole and 1-isobutyl-2-methylimidazolium can be mentioned. An imidazolium having a high polarity nitrile group such as 1-cyanoethyl-2-methylimidazolium, 1-cyanoethyl-2-undecylimidazolium, 1-cyanoethyl-2-ethyl-4-methylimidazolium, 1-cyanoethyl-2-phenylimidazolium and the like can be mentioned as an example.

Regarding the organic salt, it is preferable that E and G have a carbon-nitrogen double bond. As a specific example of the positive ion of the general formula (2), a pyridinium which may have a substituent group, a pyridazinium which may have a substituent group, a pyrimidinium which may have a substituent group and a triazinium which may have a substituent group can be mentioned. Here, regarding the organic salt constituted of the pyridinium ion, it is necessary to increase an electron density at the nitrogen atom of a neutral pyridine when the pyridinium is changed into the neutral pyridine, in order to improve the function as the curing agent or as the curing accelerator. Specifically, for example, it is preferable that the electron-donating group such as an amino group which may have a substituent group on the nitrogen atom, an alkoxy group, a hydroxy group and the like is bonded to any one of carbon atoms constituting the pyridine skeleton.

Regarding the organic salt, it is preferable that M and Q have a carbon-nitrogen double bond. As a specific example of the positive ion of the general formula (4), for example, a pyridinium which may have a substituent group, a pyridazinium which may have a substituent group, a pyrimi-dinium which may have a substituent group and a triazinium which may have a substituent group can be mentioned. Here, regarding the organic salt structured with the pyridinium ion, it is necessary to increase an electron density at the nitrogen atom of a neutral pyridine when the pyridinium is changed into the neutral pyridine, in order to improve the function as the curing agent or as the curing accelerator. Specifically, for example, it is preferable that an electron-donating group such as an amino group which may have a substituent group on the nitrogen atom, an alkoxy group, a hydroxy group and the like is bonded to any one of carbon atoms constituting the pyridine skeleton.

An organic salt according to some of the embodiments of the present invention is represented by the following general formula (5), (6), (7) or (8).

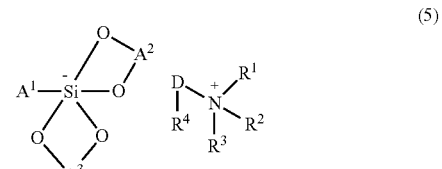

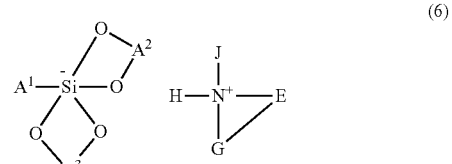

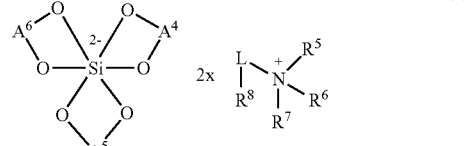

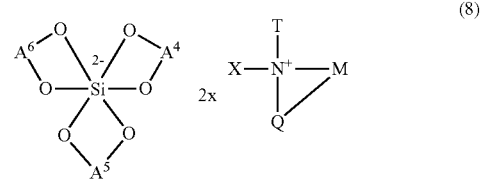

Here, [In the general formulas (5) to (8), $A^1$ represents: a hydrogen atom; a substituent group having a heteroatom of an atom of group 16 element such as an oxygen atom and a sulfur atom, an atom of group 15 element such as a nitrogen atom and a phosphorus atom, an atom of group 14 element other than a carbon atom such as a silicon atom or a halogen atom; or an organic group which may have a substituent group. $A^2$ to $A^6$ represent: independently from each other, a substituent group having a heteroatom of an atom of group 16 element such as an oxygen atom and a sulfur atom, an atom of group 15 element such as a nitrogen atom and a phosphorus atom, an atom of group 14 element other than a carbon atom such as a silicon atom or a halogen atom; or an organic group which may have a substituent group, the organic group having at least one atom bonded to two different oxygen atoms. D and L in the general formulas (5) to (8) represent: a substituent group having a heteroatom of an atom of group 15 element such as a nitrogen atom and a phosphorus atom, an atom of group 14 element other than a carbon atom such as a silicon atom or a halogen atom; or an organic group which may have a substituent group. Each of E, G, M and Q represents: independently from each other, a substituent group having a heteroatom of an atom of group 15 element such as a nitrogen atom and a phosphorus atom, an atom of group 14 element other than a carbon atom such as a silicon atom or a halogen atom; or an organic group which may have a substituent group. Each of H, J, T and X represents: independently from each other, a hydrogen atom; a substituent group having a heteroatom of an atom of group 15 element such as a nitrogen atom and a phosphorus atom, an atom of group 14 element other than a carbon atom such as a silicon atom or a halogen atom; or an organic group which may have a substituent group. Each of $R^1$ to $R^8$ in the afore-mentioned general formulas represents: a hydrogen atom; a substituent group having a heteroatom of an atom of group 15 element such as a nitrogen atom and a phosphorus atom, an atom of group 14 element other than a carbon atom such as a silicon atom or a halogen atom; or an organic group which may have a substituent group.]

Regarding the general formulas (1) and (3), it is further preferable that $R^1$ and $R^5$ are each a hydrogen atom. It is further preferable that $R^2$, $R^3$, $R^4$, and $R^5$ are each an alkyl group. It is further preferable that D and L are a methylene group. It is preferable that $R^4$ and $R^8$ are each an aryl group which may have a substituent group. Typically, $R^4$ and $R^8$ are each a phenyl group or a naphthyl group which may have a substituent group.

Regarding the organic salt, it is preferable that each of $A^2$ to $A^6$ has two carbon atoms being bonded to each other.

Regarding the organic salt, it is preferable that the two carbon atoms are bonded to different oxygen atoms, respectively.

Regarding the organic salt, it is preferable that each of $A^2$ to $A^6$ is an aryl group which may have a substituent group.

Regarding the organic salt, it is preferable that $A^1$ is a hydrogen atom, a halogen atom, or an organic group such as an aryl group which may have a substituent group, an allyl group which may have a substituent group or a vinyl group which may have a substituent group, and the like.

Regarding the organic salt, specific examples of $A^2$ to $A^6$ are represented by the following general formulas. Each of $R^9$ to $R^{13}$ in the general formulas (9) to (13) is at least one substituent group which may be the same or different from each other, and represents: a hydrogen atom; a substituent group having a heteroatom of an atom of group 16 element such as an oxygen atom and a sulfur atom, an atom of group 15 element such as a nitrogen atom and a phosphorus atom, an atom of group 14 element other than a carbon atom such as a silicon atom or a halogen atom; or an organic group which may have a substituent group. Each of $R^9$ to $R^{13}$ represents two or more substituent groups which may be the same or different from each other, and may have: a hydrogen atom; a heteroatom of an atom of group 16 element such as an oxygen atom and a sulfur atom, an atom of group 15 element such as a nitrogen atom and a phosphorus atom, an atom of group 14 element other than a carbon atom such as a silicon atom or a halogen atom; or a substituent group.

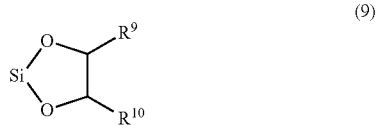

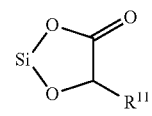

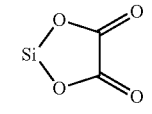

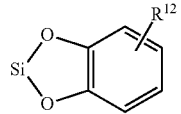

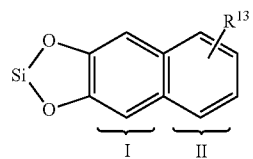

A highly-coordinated silicon compound of pentacoordinate or more having the structure represented by the general formula (9) can be synthesized for example from an alkane diol or a salt thereof which may have a substituent group as a starting material. A highly-coordinated silicon compound of pentacoordinate or more having the structure represented by the general formula (10) can be synthesized for example from a glycolic acid or a salt thereof as a starting material. A highly-coordinated silicon compound of pentacoordinate or more having the structure represented by the general formula (11) can be synthesized for example from an oxalic acid or a salt thereof as a starting material. A highly-coordinated silicon compound of pentacoordinate or more having the structure represented by the general formula (12) can be synthesized for example from a catechol or a salt thereof which may have a substituent group as a starting material. The highly-coordinated silicon compound of pentacoordinate or more having the structure represented by the general formula (12) can be synthesized for example from a compound such as a catechol derivative and a pyrogallol derivative which have two or more hydroxy groups on the benzene ring and may have a substituent group other than the hydroxy group on the benzene ring, or a salt of such compounds as a starting material. A highly-coordinated silicon compound of pentacoordinate or more having the structure represented by the general formula (13) can be synthesized for example from a compound such as a dihydroxy derivative which has two or more hydroxy groups and may have a substituent group other than the hydroxy group on a condensed hydrocarbon ring such as a naphthalene or a salt of such compound as a starting material. Substituent group $R^{13}$ may be at a side of the benzene ring (I) bonded to two oxygen atoms, and a position of a heteroatom such as the oxygen atom bonded to the silicon atom can be appropriately selected among the carbon atoms constituting the condensed hydrocarbon ring skeleton.

The catechol derivative has a structure in which the carbon atoms, to which the two hydroxy groups are bonded, are bonded with each other. Such structure allows improvement in the adhesion characteristics. Among organic salts according to the present invention, an organic salt having a catechol derivative as a ligand on the silicon atom is decomposed by heating and the like to release the silicon atom from the catechol derivative, thereby generate a free catechol derivative. When the organic salt of the catechol derivative according to the present invention is used as a curing agent or a curing accelerator of a composition for an adhesive agent, the shear adhesion strength of a cured film formed by heating tends to increase.

Here, a compound in which at least one of the carbon atoms constituting the benzene ring in the general formula (12) is substituted with a heteroatom such as a nitrogen atom, an oxygen atom, a sulfur atom and the like can also be used.

As a typical example of a compound having a heteroatom within the structure of the general formula (12), a structure having a pyridine ring represented by the following general formulas (14) and (15) can be mentioned. Regarding formula (14), the silicon atom is bonded to the oxygen atoms bonded to the 2-position and 3-position of the pyridine ring. Regarding formula (15), the silicon atom is bonded to the oxygen atoms bonded to the 3-position and 4-position of the pyridine ring.

Other typical example of a compound having a heteroatom within the structure of the general formula (12) may have, a structure having a pyrimidine ring skeleton in which two carbon atoms included in the benzene ring is replaced with two nitrogen atoms, and one carbon atom is placed between the two nitrogen atoms, such as a structure represented by the following formula (16).

Other typical example of a compound having a heteroatom within the structure of the general formula (12) may have, a structure having a pyrazine ring skeleton in which two carbon atoms included in the benzene ring is replaced with two nitrogen atoms, and two carbon atoms are placed between the two nitrogen atoms, such as a structure represented by the following formula (17).

Other typical example of a compound having a heteroatom within the structure of the general formula (12) may have, a structure having a pyridazine ring skeleton in which two carbon atoms included in the benzene ring is replaced with two nitrogen atoms, the two carbon atoms being bonded to each other, such as a structure represented by the following formulas (18) and (19). Regarding the structure of formula (18), the silicon atom is bonded to the oxygen atoms bonded to the 2-position and 3-position of the pyridazine ring. Regarding the structure of formula (19), the silicon atom is bonded to the oxygen atoms bonded to the 3-position and 4-position of the pyridazine ring.

Each of $R^{14}$ to $R^{19}$ of the following general formulas (14) to (19) is a substituent group which may be the same or different from each other, and represents: a hydrogen atom; a substituent group having a heteroatom of an atom of group 16 element such as an oxygen atom and a sulfur atom, an atom of group 15 element such as a nitrogen atom and a phosphorus atom, an atom of group 14 element other than a carbon atom such as a silicon atom or a halogen atom; or an organic group which may have a substituent group. Each of $R^9$ to $R^{13}$ represents two or more substituent groups which may be the same or different from each other, and may have: a hydrogen atom; a heteroatom of an atom of group 16 element such as an oxygen atom and a sulfur atom, an atom of group 15 element such as a nitrogen atom and a phosphorus atom, an atom of group 14 element other than a carbon atom such as a silicon atom or a halogen atom; or a substituent group.

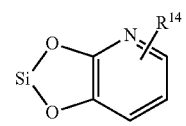

(14)

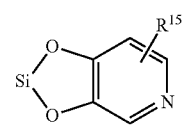

(15)

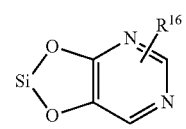

(16)

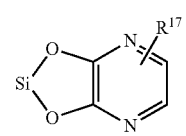

(17)

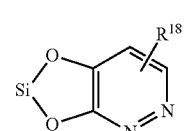

(18)

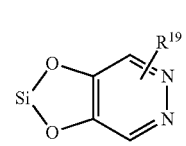

(19)

Here, a compound in which at least one of the carbon atoms constituting the naphthalene ring in the general formula (13) is substituted with a heteroatom such as a nitrogen atom, an oxygen atom, a sulfur atom, and the like can also be used.

As a typical example of a compound having a heteroatom within a structure of the general formula (13), a structure having a quinoline skeleton represented by the following general formula (20), a quinozaline skeleton represented by the following general formula (21), a quinazoline skeleton represented by the following general formula (22), a naphthyridine skeleton represented by the following general formula (23), and an isoquinoline skeleton represented by the following general formula (24) can be mentioned. In the partial structure represented by the following general formulas (20) to (24), the heteroatom such as the two oxygen atoms, to which the silicon atom is bonded, can be appropriately selected among a plurality of carbon atoms which constitute the hydrocarbon condensed ring including at least one of the quinoline skeleton, quinozaline skeleton, quinazoline skeleton, naphthyridine skeleton, isoquinoline skeleton and the like.

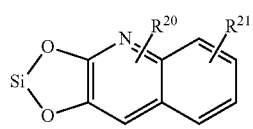

(20)

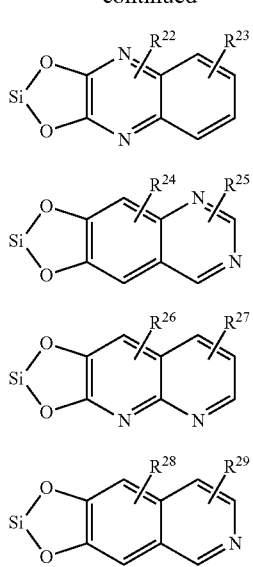

Each of R²⁰ to R²⁹ in the general formulas (20) to (24) is at least one substituent group which may be the same or different from each other, and represents: a hydrogen atom; a substituent group having a heteroatom of an atom of group 16 element such as an oxygen atom and a sulfur atom, an atom of group 15 element such as a nitrogen atom and a phosphorus atom, an atom of group 14 element other than a carbon atom such as a silicon atom or a halogen atom; or an organic group which may have a substituent group. Each of R²⁰ to R²⁹ represent two or more substituent groups which may be the same or different from each other, and is: a hydrogen atom; a substituent group having a heteroatom of an atom of group 16 element such as an oxygen atom and a sulfur atom, an atom of group 15 element such as a nitrogen atom and a phosphorus atom, an atom of group 14 element other than a carbon atom such as a silicon atom or a halogen atom; or an organic group which may have a substituent group.

The composition according to some of the embodiments of the present invention comprises any one of the base generators, any one of the reagents or any one of the organic salts, and a monomer or a resin.

Regarding the composition, it is preferable that the monomer or the resin has a ring structure, and the ring structure has a fourth atom of group 16 element.

Regarding the composition, it is preferable that the monomer or the resin has an epoxy group or an oxetanyl group.

Regarding the composition, it is preferable that the composition further comprises a compound having a hydroxy group.

Regarding the composition, it is preferable that the monomer or the resin has a silicon atom. A specific example of the monomer or the resin is, for example, a siloxane compound having a silicon-oxygen bond and an alkoxysilane compound having one or more alkoxy group.

Regarding the composition, it is preferable that the composition further comprises a particle such as a filler and the like.

Regarding the composition, it is preferable that the particle is an inorganic particle.

A method for manufacturing an device according to some of the embodiments of the present invention comprises the steps of: a first step of forming a first film by coating any one of the composition or a solution of the composition; and a second step of curing the first film or a second film by a heating step of the first film or the second film at a temperature of 50° C. or higher, the second film being a film obtained by removing at least a part of a volatile component from the first film.

Regarding the manufacturing method of the device, it is preferable that the heating step is performed by heating the first film or the second film at a temperature of 80° C. or higher.

Regarding the manufacturing method of the device, it is preferable that the heating step is performed at a temperature of 110° C. or lower.

A cured film according to some of the embodiments of the present invention is obtained by curing any one of the afore-mentioned composition.

A device according to some of the embodiments of the present invention comprises the afore-mentioned cured film.

As the positive ion, for example, a mono-substituted ammonium such as phenylammonium, ethylammonium, n-propylammonium, sec-propylammonium, n-butylammonium, sec-butylammonium, i-butylammonium, tert-butylammonium, pentylammonium, hexylammonium, heptylammonium, octylammonium, decylammonium, laurylammonium, 1,2-dimethylhexylammonium, 3-pentylammonium, 2-ethylhexylammonium, allylammonium, 1-hydroxyethylammonium, 1-hydroxyammonium, 1-methyl-2-hydroxyethylammonium, 4-hydroxybutylammonium, 1-hydroxypentylammonium, 1-hydroxyhexylammonium, 3-ethoxypropylammonium, 3-propoxypropylammonium, 3-isopropoxypropylammonium, 3-butoxypropylammonium, 3-isobutoxypropylammonium, 3-(2-ethylhexyloxy)propylammonium, cyclopentylammonium, cyclohexylammonium, norbornylammonium, cyclohexylmethylammonium, phenylammonium, benzylammonium, phenethylammonium, α-phenylethylammonium, naphthylammonium, furfurylammonium and the like; a polyvalent ammonium such as ethylenediammonium, propane-1,2-diammonium, propane-1,3-diammonium, butane-1,2-diammonium, butane-1,3-diammonium, butane-1,4-diammonium, pentane-1,5-diammonium, hexane-1,6-diammonium, heptane-1,7-diammonium, octane-1,8-diammonium, cyclohexane-1,4-diammonium, polyethyeleneimine which is a polymer and the like; a di-substituted ammonium such as diethylammonium, dipropylammonium, di-n-butylammonium, di-sec-butylammonium, diisobutylammonium, di-n-pentylammonium, di-3-pentylammonium, dihexylammonium, octylammonium, di(2-ethylhexyl)ammonium, methylhexylammonium, diallylammonium, diphenylammonium, methylphenylammonium, ethylphenylammonium, dibenzylammonium, methylbenzylammonium, dinaphthylammonium and the like; a tertiary amine such as trimethylammonium, triethylammonium, tri-n-propylammonium, tri-iso-propylammonium, tri-1,2-dimethylpropylammonium, tri-3-methoxypropylammonium, tri-n-butylammonium, triisobutylammonium, tri-sec-butylammonium, tripentylammonium, tri-3-pentylammonium, tri-n-hexylammonium, tri-n-octylammonium, tri-2-ethylhexylammonium, tridodecylammonium, trilaurylammonium, dicyclohexylethylammonium, cyclohexyldiethylammonium, tricyclohexylammonium, N,N-dimethylhexylammonium, N-methyldihexylammonium, N,N-dimethylcyclohexylammonium, N-methyldicyclohexylammonium, N,N-diethylethanolammonium, N,N-dimehtylethanolammonium, N-ethyldiethanolammonium, triethanolammonium, tribenzylammonium, N,N-dimethylphenylammonium, N,N-dimethylbenzylammonium, diethylbenzylammonium, triphenylammonium and the like; and guanidinium, biguanidinium and the like which may have a substituent group or may have a ring structure; can be mentioned. The positive ion can also be an unsubstituted pyridinium salt, and a pyridinium having at least one electron donating substituent group such as an amino group, an alkoxy group, an alkyl group, a hydroxy group and the like on the pyridine ring, such as 4-aminopyridinium, 4-methoxypyridinium, 4-methylpyridininum, N,N-dimethyl-4-aminopyridine (DMAP), 4-hydroxypyridinium and the like.

Among the ammoniums exemplified above, phenylamine having a nitrogen atom directly bonded to an unsubstituted benzene such as aniline which is a precursor of phenylammonium and N,N-dimethylphenylamine which is a precursor of N,N-dimethylphenylammonium; and unsubstituted pyridine which is a precursor of pyridinium are low in curing accelerating characteristics itself. Accordingly, there is a case where it is not necessary to positively constitute an organic salt with an anion having a highly-coordinated silicon structure, in order to use it as a curing agent or as a curing accelerator of a one-pack resin curing agent. Here, such organic salt can be, for example, used as a curing retarder to delay curing.

Here, when an organic salt is constituted with a cation and an anion; the cation having two primary amino groups in one molecule or a primary amino group and a secondary amino group in one molecule such as 4-(aminomethyl)piperidine, 3-diaminopropane and 4,4'-diamino-3,3'-diethyldiphenylmethane, being protonated to form a divalent cation; and the anion having a hexa-coordinated silicon structure, an organic salt will still be constituted even when a proton is eliminated from one of the ammonium groups in the molecule by heating and the like to generate a neutral amino group. Accordingly, a movement of the neutral amino group would be restricted, and thus the thermal curing acceleration characteristics may be degraded. Such organic salt can also be used as a curing retarder to delay curing in a similar manner.

A superbase of which conjugate acid has a pKa of 21 or higher in acetonitrile solution such as 1,4-diazabicyclo[2.2.2]octane (DABCO), diazabicyclononene (DBN), diazabicycloundecene (DBU), 1,1,3,3-tetramethylguanidine (TMG), 7-methyl-1,5,7-triazabicyclo[4.4.0]deca-5-ene (MTBD), 1,5,7-triazabicyclo[4.4.0]deca-5-ene (TBD), tert-butylimino-tri(pyrrolidino)phosphorane (BTPP), 2-tert-butylimino-2-diethylamino-1,3-dimethylperhydro-1,3,2-diazaphospholine (BEMP) and the like can be used.

As the positive ion of the compound represented by the general formulas (4), (6) and (8), an imidazole-type ion represented by the following general formula (25) having relatively superior low-temperature curing characteristics and having high glass transition temperature when a cured substance is formed, is preferable.

In fact, as can be seen from Table 1 described hereinafter, a cured film obtained by using an organic salt according to the present invention having a positive ion derived from an imidazole derivative as a curing accelerator has a high glass transition temperature. In addition, as can be seen from a comparison with the Comparative Example, when an organic salt having a catechol derivative represented by the general formulas (12) and (13) as a ligand of the negative ion is used as the curing accelerator, the glass transition temperature rises even when the positive ion is the same imidazolium.

That is, by using the catechol derivative as the ligand constituting the highly-coordinated silicon structure and using imidazolium for the positive ion side, a high glass transition temperature can be achieved. Since high glass transition temperature has a positive correlation with the sealing characteristics, it can be said that an organic salt of the catechol derivative-type highly-coordinated silicon anion and the imidazole derivative cation is a superior polymerization catalyst of a resin.

Each of $R^{30}$ to $R^{34}$ in the general formula (25) is independent from each other and represents a substituent group which may be the same or different from each other, and represents: a hydrogen atom; a substituent group having a heteroatom of an atom of group 16 element such as an oxygen atom and a sulfur atom, an atom of group 15 element such as a nitrogen atom and a phosphorus atom, an atom of group 14 element other than a carbon atom such as a silicon atom or a halogen atom; or an organic group which may have a substituent group. Further, it is preferable that $R^{30}$ is a hydrogen atom. In addition, $R^{31}$ and $R^{32}$ may form a ring structure by bonding with each other via at least one bond, or $R^{33}$ and $R^{34}$ may form a ring structure by bonding with each other via at least one bond. Here, a compound having at least one carbon atom in the five-membered ring of the imidazolium of general formula (25), the carbon atom being substituted with a heteroatom such as a sulfur atom, an oxygen atom and the like, can be used. For example, the carbon atom positioned between the two nitrogen atoms of the five-membered ring may be substituted with a sulfur atom, thereby improving acid resistance of the cured film obtained by curing a substrate such as an epoxy compound with the present organic salt.

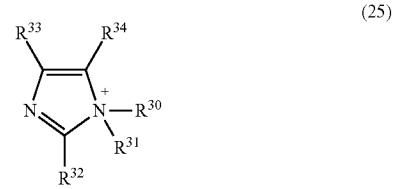

(25)

As a positive ion of a compound represented by the general formulas (4), (6) and (8), a monovalent positive ion having a plurality of amino groups in one molecule, one of such plurality of amino groups being protonated to constitute an ammonium group, such as represented by the following general formulas (26) to (28), can be mentioned. In a specific example, following general formula (26) is a piperazinium having a ring structure, and following general formula (27) is N,N-dimethylpiperazinium having a ring structure. In addition, in the following general formula (28), one of the amino groups of the triethylenediamine is protonated.

(26)

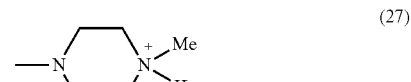

(27)

(28)

As a positive ion of a compound represented by the general formulas (4), (6) and (8), such as represented by the following general formulas (29) and (30), a positive ion having a plurality of nitrogen atoms, at least two of the plurality of nitrogen atoms being bonded to an aromatic ring, one nitrogen atom among the at least two nitrogen atoms being protonated, can be mentioned.

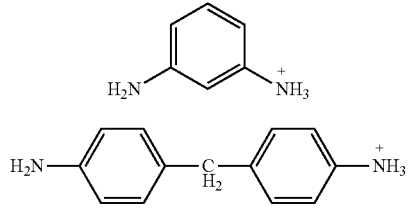

(29)

(30)

As a preferable example of the positive ion of the general formulas (1), (3), (5) and (7), a positive ion having an aryl alkyl group on a nitrogen atom can be mentioned. The following organic salts 1, 13, 21, 22, 23 and the like having a monovalent positive ion having an aryl alkyl group such as an aryl methyl group on the nitrogen atom can polymerize an epoxy compound even in a low temperature range of 80 to 110° C. In addition to the aryl methyl group, the positive ion may have at least one organic group. As a more specific example, N,N-dimethylbenzylammonium represented by the following general formula (31), 2-dimethylaminomethylphenol represented by the following general formula (32) and 2,4,6-tris(dimethylaminomethyl)phenol represented by the following general formula (33) can be mentioned.

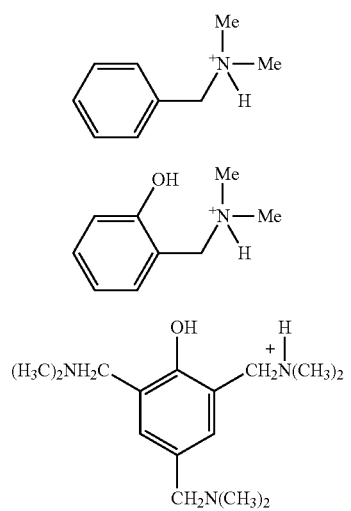

(31)

(32)

(33)

As a preferable example of a negative ion of the organic salts of general formulas (1) to (8), a structure represented by the following general formula (35) can be mentioned. $R^{35}$ is at least one or more substituent group, which may be the same or different from each other, and represent: a hydrogen atom; a substituent group having a heteroatom of group 16 element such as an oxygen atom and a sulfur atom, an atom of group 15 element such as a nitrogen atom and a phosphorus atom, an atom of group 14 element such as a silicon atom or a halogen atom; or an organic group which may have a substituent group.

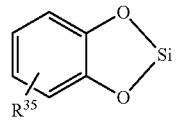

(35)

An especially preferable substituent group is a hydroxy group, an alkoxy group, a carboxyl group, an ester group, a cyano group and an alkyl group. Among them, the hydroxy group can contribute to improvement in shelf stability since it can trap a base such as amines which is released from the organic salt. In addition, the alkyl group and the ester group can suppress aggregation of the organic salt by their steric hindrance. Accordingly, dispersibility in a liquid composition can be improved. Further, since approach of the organic salt and the substrates such as the resin and the monomer is suppressed, both of the shelf stability and the curing characteristics can be achieved.

As the alkyl group used for such organic salt, a linear or branched alkyl group which may have a substituent group having a heteroatom can be mentioned. Here, as in the examples of the organic salts 17, and 20 to 23, dispersibility can be improved by using a substituent group with a large steric hindrance such as tert-butyl group.

As the ester group, an ester group having a linear or branched alkyl group which may have a substituent group having a heteroatom can be mentioned. Here, as in the organic salt 24 described hereinafter, an ester group having a linear alkyl group can be used. Of course, it is possible to appropriately combine the aforementioned substituent groups.

DESCRIPTION OF EMBODIMENTS

Hereinafter, preferable embodiments of the present invention will be described.

Synthesis of a typical organic salt according to some embodiments of the present invention is performed by a step involving a reaction of a compound having at least two or more hydroxyl groups and optionally other substituent group and a silane compound having three or more alkoxy groups on one silicon atom, in the presence of a base such as an amine.

To a separable flask (volume: 500 mL) equipped with a cooling tube and a stirrer, 22.0 g (0.20 mol) of catechol, 24.0 g (0.10 mol) of phenyltriethoxysilane and 50 mL of methanol are added, and the mixture is stirred to obtain a homogeneous solution. Subsequently, a solution prepared by dissolving 10.7 g (0.10 mol) of benzylamine in 10 mL of methanol is added dropwise to the flask with stirring. After allowing the reaction to proceed for 2 hours at room temperature, 20 mL of isopropyl ether is added to the separable flask to precipitate a crystal. Then, the precipitated crystal is filtered, rinsed and dried under vacuum to purify, and to obtain organic salt 1 represented by the following general formula 36.

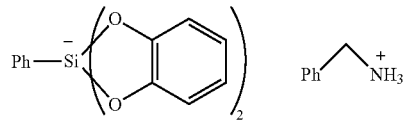

(36)

To a separable flask (volume: 500 mL) equipped with a cooling tube and a stirrer, 22.0 g (0.20 mol) of catechol, 24.0 g (0.10 mol) of phenyltriethoxysilane and 50 mL of methanol are added, and the mixture is stirred to obtain a homogeneous solution. Subsequently, a solution prepared by dissolving 6.81 g (0.10 mol) of imidazole in 10 mL of methanol is added dropwise to the flask with stirring. After allowing the reaction to proceed for 2 hours at room temperature, 20 mL of isopropyl ether is added to the separable flask to precipitate a crystal. Then, the precipitated crystal is filtered, rinsed and dried under vacuum to purify, and to obtain organic salt 2 represented by the following general formula 37.

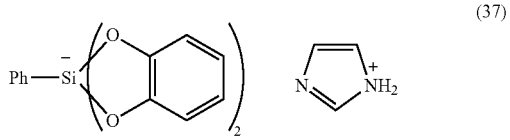

(37)

To a separable flask (volume: 500 mL) equipped with a cooling tube and a stirrer, 22.0 g (0.20 mol) of catechol, 24.0 g (0.10 mol) of phenyltriethoxysilane and 50 mL of methanol are added, and the mixture is stirred to obtain a homogeneous solution. Subsequently, a solution prepared by dissolving 8.21 g (0.10 mol) of 2-methylimidazole in 10 mL of methanol is added dropwise to the flask with stirring. After allowing the reaction to proceed for 2 hours at room temperature, 20 mL of isopropyl ether is added to the separable flask to precipitate a crystal. Then, the precipitated crystal is filtered, rinsed and dried under vacuum to purify, and to obtain organic salt 3 represented by the following general formula 38.

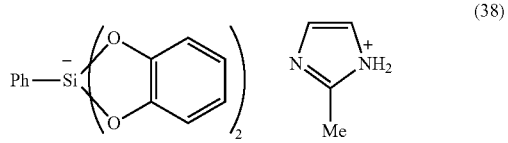

(38)

To a separable flask (volume: 500 mL) equipped with a cooling tube and a stirrer, 33.0 g (0.30 mol) of catechol, 20.1 g (0.10 mol) of tetraethoxysilane and 50 mL of methanol are added, and the mixture is stirred to obtain a homogeneous solution. Subsequently, a solution prepared by dissolving 21.4 g (0.20 mol) of benzylamine in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 4 represented by the following general formula 39.

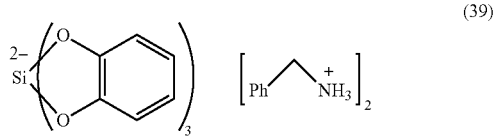

(39)

To a separable flask (volume: 500 mL) equipped with a cooling tube and a stirrer, 33.0 g (0.30 mol) of catechol, 20.1 g (0.10 mol) of tetraethoxysilane and 50 mL of methanol are added, and the mixture is stirred to obtain a homogeneous solution. Subsequently, a solution prepared by dissolving 13.6 g (0.20 mol) of imidazole in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 5 represented by the following general formula 40.

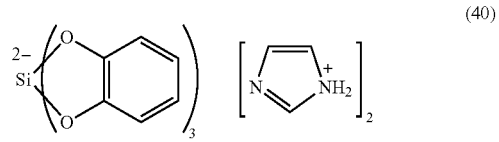

(40)

To a separable flask (volume: 500 mL) equipped with a cooling tube and a stirrer, 33.0 g (0.30 mol) of catechol, 20.1 g (0.10 mol) of tetraethoxysilane and 50 mL of methanol are added, and the mixture is stirred to obtain a homogeneous solution. Subsequently, a solution prepared by dissolving 16.4 g (0.20 mol) of 2-methylimidazole in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 6 represented by the following general formula 41.

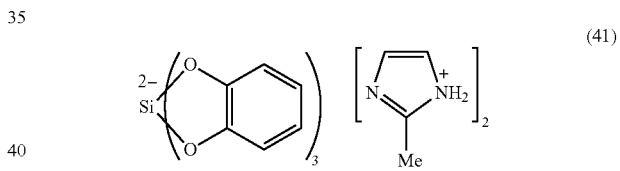

(41)

To a separable flask (volume: 500 mL) equipped with a cooling tube and a stirrer, 37.8 g (0.30 mol) of pyrogallol, 20.1 g (0.10 mol) of tetraethoxysilane and 50 mL of methanol are added, and the mixture is stirred to obtain a homogeneous solution. Subsequently, a solution prepared by dissolving 16.4 g (0.20 mol) of 2-methylimidazole in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 7 represented by the following general formula 42.

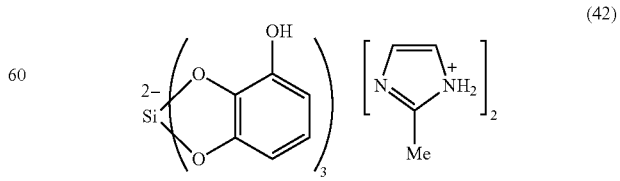

(42)

To a separable flask (volume: 500 mL) equipped with a cooling tube and a stirrer, 37.8 g (0.30 mol) of pyrogallol, 20.1 g (0.10 mol) of tetraethoxysilane and 50 mL of methanol are added, and the mixture is stirred to obtain a homogeneous solution. Subsequently, a solution prepared by dissolving 13.6 g (0.20 mol) of imidazole in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 8 represented by the following general formula 43.

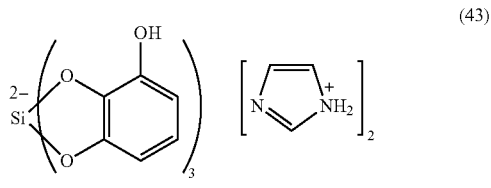

(43)

To a separable flask (volume: 500 mL) equipped with a cooling tube and a stirrer, 37.8 g (0.30 mol) of pyrogallol, 20.1 g (0.10 mol) of tetraethoxysilane and 50 mL of methanol are added, and the mixture is stirred to obtain a homogeneous solution. Subsequently, a solution prepared by dissolving 19.2 g (0.20 mol) of 1,2-dimethylimidazole in 10 mL of methanol are added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 9 represented by the following general formula 44.

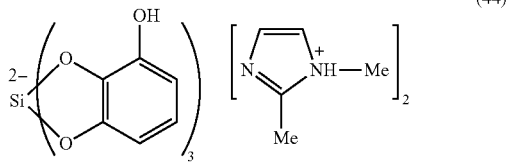

(44)

To a separable flask (volume: 500 mL) equipped with a cooling tube and a stirrer, 22.0 g (0.20 mol) of catechol, 24.0 g (0.10 mol) of phenyltriethoxysilane and 50 mL of methanol are added, and the mixture is stirred to obtain a homogeneous solution. Subsequently, a solution prepared by dissolving 9.4 g (0.10 mol) of 4-aminopyridine in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 10 represented by the following general formula 45.

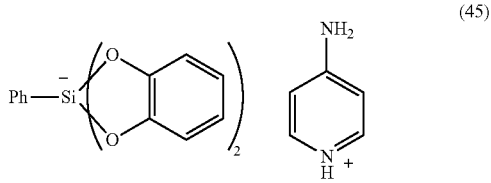

(45)

To a separable flask (volume: 500 mL) equipped with a cooling tube and a stirrer, 22.0 g (0.20 mol) of catechol, 24.0 g (0.10 mol) of phenyltriethoxysilane and 50 mL of methanol are added, and the mixture is stirred to obtain a homogeneous solution. Subsequently, a solution prepared by dissolving 8.5 g (0.10 mol) of piperidine as a secondary amine in 10 mL of methanol is added dropwise to the flask with stirring. After allowing the reaction to proceed for 2 hours at room temperature, 20 mL of isopropyl ether is added to the separable flask to precipitate a crystal. Then, the precipitated crystal is filtered, rinsed and dried under vacuum to purify, and to obtain organic salt 11 represented by the following general formula 46.

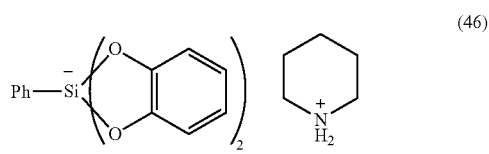

(46)

To a separable flask (volume: 500 mL) equipped with a cooling tube and a stirrer, 37.8 g (0.30 mol) of pyrogallol, 20.1 g (0.10 mol) of tetraethoxysilane and 50 mL of methanol are added, and the mixture is stirred to obtain a homogeneous solution. Subsequently, a solution prepared by dissolving 23.3 g (0.20 mol) of tetramethyl guanidine in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 12 represented by the following general formula 47.

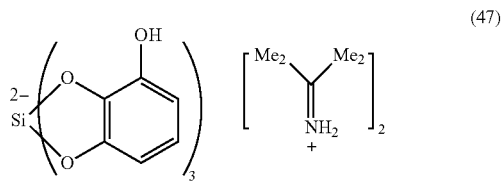

(47)

To a separable flask (volume: 500 mL) equipped with a cooling tube and a stirrer, 33.0 g (0.30 mol) of catechol, 20.1 g (0.10 mol) of tetraethoxysilane and 50 mL of methanol are added, and the mixture is stirred to obtain a homogeneous solution. Subsequently, a solution prepared by dissolving 27.0 g (0.20 mol) of N,N-dimethylbenzylamine as a tertiary amine in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 13 represented by the following general formula 48.

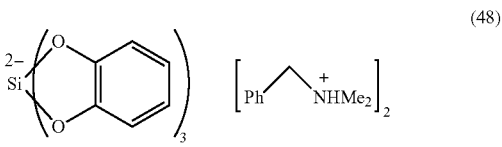

(48)

To a separable flask (volume: 500 mL) equipped with a cooling tube and a stirrer, 33.0 g (0.30 mol) of catechol, 20.1 g (0.10 mol) of tetraethoxysilane and 50 mL of methanol are added, and the mixture is stirred to obtain a homogeneous solution. Subsequently, a solution prepared by dissolving 8.6 g of polyethyleneimine (PEI) having an average molecular weight of 1800 in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain polymer-type organic salt 14 represented by the following general formula 49. Here, by using a polymer such as polyethyleneimine (PEI) as the base, curing temperature can be raised. Accordingly, when a thermal-curing test was performed by using 25 parts by mass of the present organic salt with respect to 100 parts by mass of a bisphenol A-type epoxy resin (jER828, manufactured by Mitsubishi Chemical Corporation), curing proceeded at a curing temperature of 180° C. or higher.

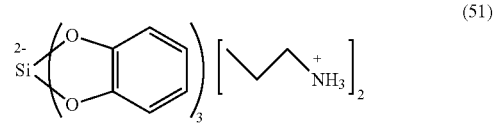
(49)

To a separable flask (volume: 500 mL) equipped with a cooling tube and a stirrer, 37.8 g (0.30 mol) of pyrogallol, 20.1 g (0.10 mol) of tetraethoxysilane and 50 mL of methanol are added, and the mixture is stirred to obtain a homogeneous solution. Subsequently, a solution prepared by dissolving 20.2 g (0.20 mol) of triethylamine in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 15 represented by the following general formula 50.

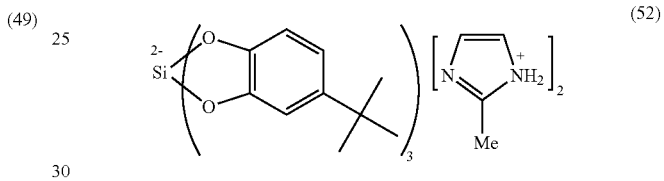
(50)

To a separable flask (volume: 500 mL) equipped with a cooling tube and a stirrer, 33.0 g (0.30 mol) of catechol, 20.1 g (0.10 mol) of tetraethoxysilane and 50 mL of methanol are added, and the mixture is stirred to obtain a homogeneous solution. Subsequently, a solution prepared by dissolving 11.8 g (0.20 mol) of propylamine in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 16 represented by the following general formula 51.

(51)

To a separable flask (volume: 500 mL) equipped with a cooling tube and a stirrer, 49.9 g (0.30 mol) of 4-tert-butyl catechol, 20.1 g (0.10 mol) of tetraethoxysilane and 50 mL of methanol are added, and the mixture is stirred to obtain a homogeneous solution. Subsequently, a solution prepared by dissolving 16.4 g (0.20 mol) of 2-methylimidazole in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 17 represented by the following general formula 52.

(52)

To a separable flask (volume: 500 mL) equipped with a cooling tube and a stirrer, 37.8 g (0.30 mol) of pyrogallol, 20.1 g (0.10 mol) of tetraethoxysilane and 50 mL of methanol are added, and the mixture is stirred to obtain a homogeneous solution. Subsequently, a solution prepared by dissolving 23.6 g (0.20 mol) of benzimidazole in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 18 represented by the following general formula 53.

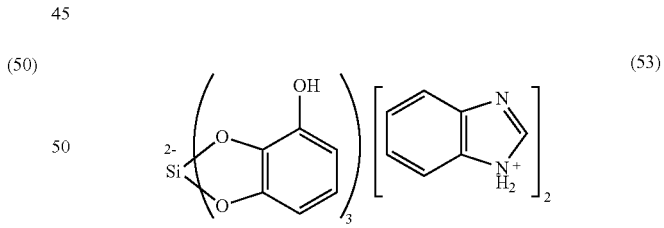
(53)

To a separable flask (volume: 500 mL) equipped with a cooling tube and a stirrer, 37.8 g (0.30 mol) of pyrogallol, 20.1 g (0.10 mol) of tetraethoxysilane and 50 mL of methanol are added, and the mixture is stirred to obtain a homogeneous solution. Subsequently, a solution prepared by dissolving 16.4 g (0.20 mol) of 1-methylimidazole in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 19 represented by the following general formula 54.

(54)

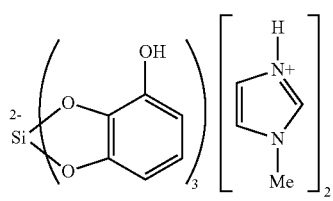

To a separable flask (volume: 500 mL) equipped with a cooling tube and a stirrer, 49.9 g (0.30 mol) of 4-tert-butyl catechol, 20.1 g (0.10 mol) of tetraethoxysilane and 50 mL of methanol are added, and the mixture is stirred to obtain a homogeneous solution. Subsequently, a solution prepared by dissolving 17.2 g (0.20 mol) of piperazine in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal were filtered, rinsed and dried under vacuum to purify, and to obtain organic salt 20 represented by the following general formula 55.

(55)

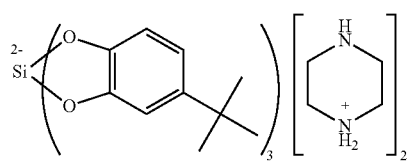

To a separable flask (volume: 500 mL) equipped with a cooling tube and a stirrer, 49.9 g (0.30 mol) of 4-tert-butyl catechol, 20.1 g (0.10 mol) of tetraethoxysilane and 50 mL of methanol are added, and the mixture is stirred to obtain a homogeneous solution. Subsequently, a solution prepared by dissolving 27.0 g (0.20 mol) of N,N-dimethylbenzylamine in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 21 represented by the following general formula 56.

(56)

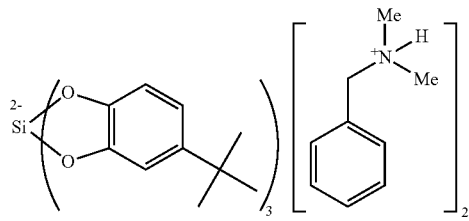

To a separable flask (volume: 500 mL) equipped with a cooling tube and a stirrer, 49.9 g (0.30 mol) of 4-tert-butyl catechol, 20.1 g (0.10 mol) of tetraethoxysilane and 50 mL of methanol are added, and the mixture is stirred to obtain a homogeneous solution. Subsequently, a solution prepared by dissolving 30.2 g (0.20 mol) of 2-dimethylaminomethylphenol in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 22 represented by the following general formula 57.

(57)

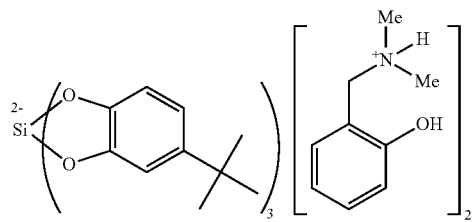

To a separable flask (volume: 500 mL) equipped with a cooling tube and a stirrer, 49.9 g (0.30 mol) of 4-tert-butyl catechol, 20.1 g (0.10 mol) of tetraethoxysilane and 50 mL of methanol are added, and the mixture is stirred to obtain a homogeneous solution. Subsequently, a solution prepared by dissolving 21.6 g (0.20 mol) of 3-picolylamine in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 23 represented by the following general formula 58.

(58)

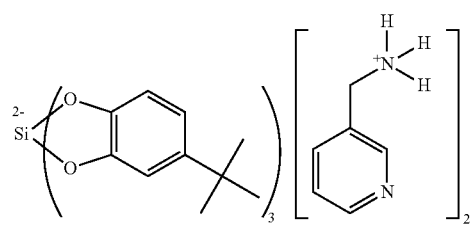

To a separable flask (volume: 500 mL) equipped with a cooling tube and a stirrer, 63.7 g (0.30 mol) of propyl gallate, 20.1 g (0.10 mol) of tetraethoxysilane and 50 mL of methanol are added, and the mixture is stirred to obtain a homogeneous solution. Subsequently, a solution prepared by dissolving 16.4 g (0.20 mol) of 2-methylimidazole in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 24 represented by the following general formula 59.

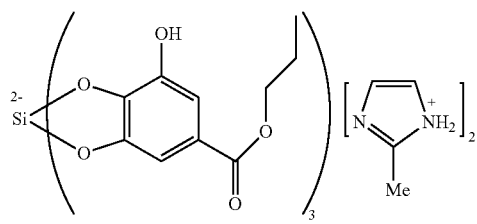

(59)

To a separable flask (volume: 500 mL) equipped with a cooling tube and a stirrer, 49.9 g (0.30 mol) of 4-tert-butyl catechol, 20.1 g (0.10 mol) of tetraethoxysilane and 50 mL of methanol are added, and the mixture is stirred to obtain a homogeneous solution. Subsequently, a solution prepared by dissolving 30.448 g (0.20 mol) of 1,8-diazabicyclo [5.4.0]-7-undecene (DBU) in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 25 represented by the following general formula 60.

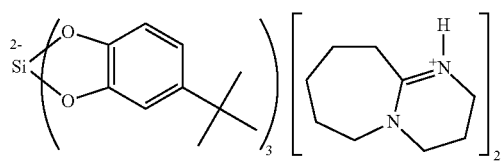

(60)

To a separable flask (volume: 500 mL) equipped with a cooling tube and a stirrer, 33.0 g (0.30 mol) of catechol, 20.1 g (0.10 mol) of tetraethoxysilane and 50 mL of methanol are added, and the mixture is stirred to obtain a homogeneous solution. Subsequently, a solution prepared by dissolving 30.448 g (0.20 mol) of 1,8-diazabicyclo[5.4.0]-7-undecene (DBU) in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 26 represented by the following general formula 61.

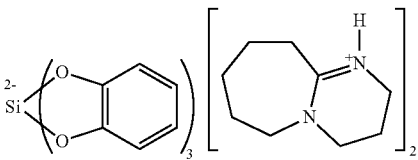

(61)

To a separable flask (volume: 500 mL) equipped with a cooling tube and a stirrer, 37.8 g (0.30 mol) of pyrogallol, 20.1 g (0.10 mol) of tetraethoxysilane and 50 mL of methanol are added, and the mixture is stirred to obtain a homogeneous solution. Subsequently, a solution prepared by dissolving 30.448 g (0.20 mol) of 1,8-diazabicyclo[5.4.0]-7-undecene (DBU) in 10 mL of methanol is added dropwise to the flask with stirring. After allowing the reaction to proceed for 1 hour at room temperature, 20 mL of isopropyl ether is added to the separable flask to precipitate a crystal. Then, the precipitated crystal is filtered, rinsed and dried under vacuum to purify, and to obtain organic salt 27 represented by the following general formula 62.

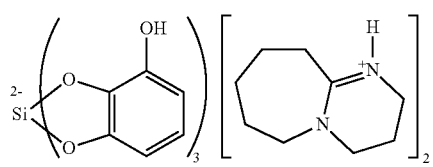

(62)

The afore-mentioned organic salts can, for example, function as a base generator which generates a base by heat or light. In addition, the afore-mentioned organic salts can function as a curing agent or as a curing accelerator which cures a monomer or a resin such as an epoxy resin, a novolac resin and a polyamic acid.

[Preparation of Composition and Manufacture of Cured Film]

To 100 parts by mass of bisphenol A-type epoxy resin (jER828, manufactured by Mitsubishi Chemical Corporation), 161 parts by mass of acid anhydride (HN-5500, manufactured by Hitachi Chemical Company, Ltd.), 14 parts by mass of the organic salt 3, 26, 25, 18, 19, 17, 20, 22, 21 or 23, 0.55 parts by mass of a silane coupling agent (KBM-403, manufactured by Shin-Etsu Chemical Co., Ltd.) are mixed and kneaded, thereby preparing a liquid composition. Gelation time and viscosity change are measured at 150° C. and at 25° C., respectively. The Comparative Example is an amine adduct of 2-methylimidazole. The liquid composition is applied between two iron sample specimens, and shear adhesion strength is measured using a tension testing machine.

TABLE 1

| Curing Accelerator | Unit | Comparative Example | 3 | 26 | 25 | 18 | 19 |
|---|---|---|---|---|---|---|---|
| Appearance | | White Opaque | White Opaque | White Opaque | White Opaque | White Opaque | White Opaque |
| Gelation Time | Sec | 180 | 220 | 120 | 190 | 190 | 140 |
| Viscosity After 24 hours (25° C.) | times | 1.25 | 1.06 | 1.41 | 1.28 | 1.26 | 1.36 |
| Uniformity (Cured Film) | | Good | Superior | Superior | Superior | Superior | Superior |

TABLE 1-continued

| | | | | | | |
|---|---|---|---|---|---|---|
| Tg (Cured Film) | °C. | 108 | 120 | 125 | 120 | 123 | 103 |
| Shear Bonding Strength of Cured Film | N/mm² | 5.20 | 8.60 | 7.50 | 7.00 | 7.30 | 16.00 |

| Curing Accelerator | Unit | 17 | 20 | 22 | 21 | 23 |
|---|---|---|---|---|---|---|
| Appearance | | White Translucent | Reddish Brown Translucent | Colorless Transparent | White Opaque | White Opaque |
| Gelation Time | Sec | 160 | 500 | 200 | 180 | 100 |
| Viscosity After 24 hours (25° C.) | times | 1.15 | 1.40 | 2.78 | 1.56 | 1.40 |
| Uniformity (Cured Film) | | Superior | Superior | Superior | Superior | Superior |
| Tg (Cured Film) | °C. | 84 | 104 | 112 | 85 | 70 |
| Shear Bonding Strength of Cured Film | N/mm² | 8.50 | 15.20 | 9.90 | 12.40 | 10.70 |

From Table 1, it can be seen that when the organic salt of the present invention is used as the curing accelerator, the shear adhesion strength becomes higher by 1.5 times compared to a case where the amine adduct of Comparative Example is used as the curing accelerator.

When organic salt 26 in which a proton adduct of DBU is the ammonium cation and a hexacoordinate silicon having three catechols as ligands is the anion is used as a powder composition for semiconductor sealing agent including a phenol resin and an epoxy resin, high shelf stability can be achieved, however, in the liquid composition, the shelf stability is not as good as such. When a substituent group such as an alkyl group is introduced on the benzene ring of the three catechol ligands as organic salt 25, the shelf stability can be improved even in the liquid composition. When there is another substituent group such as a hydroxy group in addition to the oxygen atom which coordinates to the silicon atom, the another substituent being on the benzene ring of the catechol ligand which coordinates with the silicon atom, the hydroxy group can function as a trapping site of the released DBU, and may improve the shelf stability of the liquid composition.

Comparing with the cured film of Comparative Example in Table 1, the shear strength of the cured film is improved by 1.5 times or more. This indicates that the anionic portion of the organic salt of the present invention contributes to improvement of the shear adhesion strength.

In addition, to 100 parts by mass of bisphenol A-type epoxy resin (jER828, manufactured by Mitsubishi Chemical Corporation), 8 parts by mass of dicyandiamide and 5 parts by mass of the organic salt 18 are mixed and kneaded at room temperature to prepare a liquid composition. The liquid composition is applied between two steel sample specimens, and is heated at 170° C. for 20 minutes, thereby obtaining a cured film. shear adhesion strength of the cured film is measured. The cured film obtained by using the organic salt of the present invention as the curing accelerator has at least 1.3 times or more shear adhesion strength compared with the cured film of the Comparative Example obtained by using amine adduct-type compound of 2-methylimidazole as the curing accelerator.

To 100 parts by mass of bisphenol A-type epoxy resin (jER828, manufactured by Mitsubishi Chemical Corporation), 25 parts by mass of the organic salts 3 or 18, and 0.55 parts by mass of a silane coupling agent (KBM-403, manufactured by Shin-Etsu Chemical Co., Ltd.) are mixed and kneaded at room temperature, thereby obtaining a liquid composition in which the organic salt of the present invention and the Comparative Example function as the curing agent. The liquid composition is applied between two steel sample specimens, and is heated at 100° C. for 30 minutes, thereby obtaining a cured film. Shear adhesion strength of the cured film was measured using a tension testing machine. The cured film obtained by using the organic salt of the present invention as the curing agent also showed at least 1.3 times or more shear adhesion strength compared with the cured film of the Comparative Example obtained by using amine adduct-type compound of 2-methyl imidazole as the curing agent.

As described above, by using the organic salt of the present invention as the curing agent or as the curing accelerator, the shear adhesion strength of the cured film can be improved. Accordingly, a composition including the organic salt is especially useful as an adhesive agent for electronic components such as an underfill agent which adheres a device such as a semiconductor device with another device and a substrate; and a structure adhesive agent used for manufacturing a structure such as an automobile and an architecture.

Composition A including a bisphenol A-type epoxy resin (jER828, manufactured by Mitsubishi Chemical Corporation), any one of the afore-mentioned organic salts of 1 to 13, 14 and 16 which functions as a curing agent (25 wt % with respect to the resin) and AEROSIL200 (1 wt % with respect to the resin, manufactured by EVONIK Co., Ltd.) is prepared.

Composition B including a bisphenol A-type epoxy resin (jER828, manufactured by Mitsubishi Chemical Corporation), the afore-mentioned organic salts of 13 or 15 which functions as a curing accelerator (10 wt % with respect to the resin), maleic anhydride (90 wt % with respect to the resin) and 1,4-cyclohexanedimethanol as a curing accelerator aid (10 wt % with respect to the resin) is prepared.

[Manufacture of Device]

Coating films are formed by coating the compositions A and B on substrates for wiring using an adhesive agent coating machine, and then the coating films are subjected to volume expansion at 80° C. to 150° C., 1 Torr, for 3 minutes. Subsequently, electronic components such as a 20 Pin SOIC component are installed using a component installing machine, followed by exposing the substrates at 150° C. for 5 minutes, thereby heat-curing the coating films to form substrates having an electronic circuit formed thereon.

The afore-mentioned substrate for wiring and the 20 Pin SOIC component are replaced with a glass substrate and an optical element such as a prism and a lens, respectively. In an analogous manner, the coating film of composition A and B are heat-cured to form an optical element. Many of the afore-mentioned organic salts have high transparency, and thus they are also suitable as an adhesive agent for forming optical component.

The afore-mentioned composition A and B can be discharged as a thermocuring ink from an ink jet head of a piezoelectric element ink jet head, a bubble jet (registered trademark) ink jet head, a continuous jetting ink jet head, an electrostatic induction ink jet head and the like, thereby forming a desired pattern shape. That is, the afore-mentioned compositions A and B can be made into an ink and used as a thermocuring ink to directly draw a desired pattern. A spotter can also be used for directly drawing a pattern by the thermocuring ink according to the present invention.

A compound such as a pigment, a dye and a light emitting material can be added to the thermocuring ink to display as desired on a plastic substrate such as glass and metal.

[Prepreg Resin Composition for Carbon Fiber Reinforced Plastic]

350 g of N,N,N',N'-tetraglycidyldiaminodiphenylmethane (epoxy equivalent of 120), 300 g of brominated epoxy resin (epoxy equivalent of 360), 350 g of bisphenol-A type epoxy resin (epoxy equivalent of 189, 250 g of organic salt 4 or organic salt 21 as the curing agent and 2564 g of polyethersulfone 100p (added by 20 parts) are dissolved in 3590 g of a solvent mixture of methylene chloride (55)/chloroform (42)/methanol (3). Torayca T300 cloth #7373 is impregnated with this solution, allowed to stand overnight, and is then dried at 120° C. for 5 minutes to prepare a cloth prepreg of WR41%. The prepreg is then laminated by 24-ply in a pseudo isotropic manner, and is placed on an aluminum plate being subjected to a releasement treatment. The aluminum plate with the prepreg is set for an autoclave in a nylon vacuum bag. The set bag is placed in the autoclave and pressure is applied at 6 kg/cm², followed by heating at 180° C. for 2 hours to obtain a cured plate. The cured plate has a thickness of 5.0 mm and a glass transition temperature of 190° C. From this cured plate, a test specimen is cut out by 150 mm length and 100 mm width, and then the end-face is machined so that the direction in the length thickness direction and the width thickness direction have an angle of 90 degrees. The test specimen is given a falling weight impact under the conditions of 900 kg-cm per 10 mm thickness. Subsequently, compressive load is applied in the length direction, and residual compressive strength after impact is measured. The cases where organic salt 4 and organic salt 21 are used as the curing agent have a residual compressive strength of 26.5 kg/mm² and 27.0 kg/mm², respectively. As a Comparative Example, 350 g of N,N,N', N'-tetraglycidyldiaminodiphenylmethane, 300 g of brominated epoxy resin, 350 g of bisphenol-A type epoxy resin and 470 g of neopentyl glycol bis(p-aminobenzoate) (corresponds as 1 amine equivalent with respect to 1 epoxy equivalent) are dissolved in MEK. When the residual compressive strength after impact is measured in a similar manner as above using this solution, and the residual compressive strength was 18.0 kg/mm².

The aforementioned organic salt according to some embodiments of the present invention can be used as a curing agent, a curing accelerator, a material or a base generator for preparing a composition or an ink to form a member or a film having a mechanical, chemical, optical and electronical characteristics such as a sealing member, a adhesive member, a prepreg, a rust-preventive agent, a protective film, a reflection film and an insulating film.

The aforementioned organic salt according to some embodiments of the present invention can be used as a curing agent and as a curing accelerator of a composition including a polymerizable substrate such as an epoxy compound, a phenol compound, or an isocyanate compound and an alcohol compound for preparing a urethane resin. The aforementioned organic salt according to some embodiments of the present invention is superior in view of low temperature curing characteristic, film characteristic of the cured composition (for example, such as glass transition temperature and shear adhesion strength) and shelf stability.

The aforementioned organic salts according to some embodiments of the present invention is significant in view of excellence in curing characteristic including superior film characteristic of the cured film as well as shelf stability, with respect to a solution composition being differ from a powder composition and shortening lifetime of the curing agent or the curing accelerator, or a dispersed liquid composition having dispersed particles.

The invention claimed is:

1. A curable composition comprising:
   the organic salt represented by general formula (6) or (8); and
   a monomer having an epoxy group or an oxetanyl group or a resin having an epoxy group or an oxetanyl group,

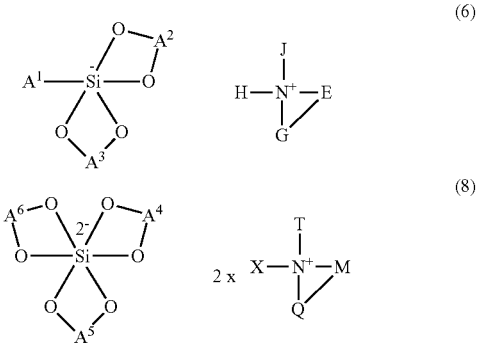

where:

A$^1$ in the general formula (6) represents: a hydrogen atom; a substituent group having an atom of a group 16 element, an atom of a group 15 element, an atom of a group 14 element other than a carbon atom or a halogen atom; or a monovalent organic group;

each of A$^2$ to A$^6$ in the general formulas (6) and (8), together with the oxygen atoms to which they are attached, represents: independently from each other, a partial structure selected from the group consisting of the general formulas (12) to (24), wherein R$^{12}$ to R$^{29}$ each represent an optional substituent group;

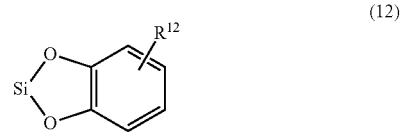

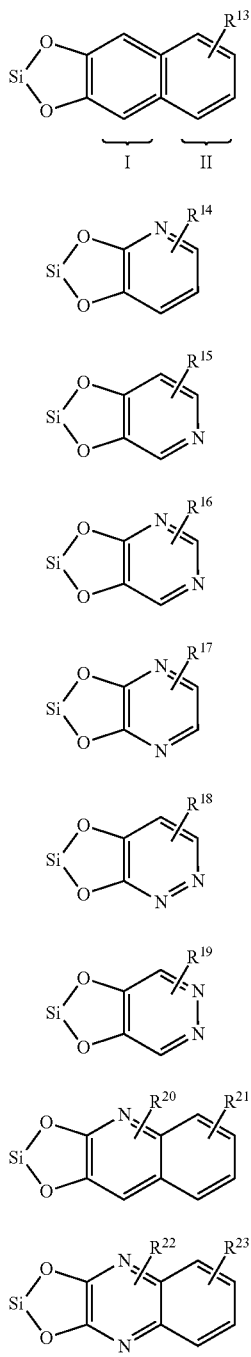

(13)
(14)
(15)
(16)
(17)
(18)
(19)
(20)
(21)

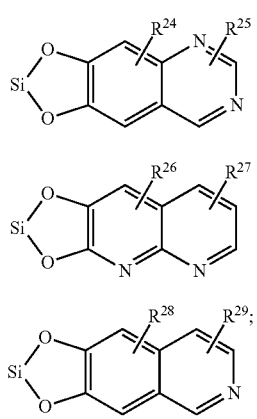

(22)
(23)
(24)

each of E, G, M and Q represents: independently from each other, a substituent group having an atom of a group 15 element, an atom of a group 14 element other than a carbon atom or a halogen atom; or a divalent organic group;

each of H, J, T and X represents: independently from each other, a hydrogen atom; a substituent group having an atom of a group 15 element, an atom of a group 14 element other than a carbon atom or a halogen atom; or a monovalent organic group; and the cations in the general formulas (6) and (8) are selected from the group consisting of an azolium cation, an imidazolium cation, a pyridazinium cation, a pyrimidinium cation, a triazinium cation and a piperazinium cation.

2. The curable composition of claim 1, further comprising a compound having a hydroxy group.

3. The curable composition of claim 1, wherein the monomer or the resin has a silicon atom.

4. The curable composition of claim 1, further comprising a particle.

5. The curable composition of claim 4, wherein the particle is an inorganic particle.

6. A method for manufacturing a device comprising:
a first step of forming a first film by applying the curable composition of claim 1 or a solution of the curable composition; and
a second step of curing the first film by a heating step of the first film at a temperature of 50° C. or higher to obtain a device.

7. A device comprising a cured film obtained by curing the curable composition of claim 1.

8. The curable composition of claim 1, wherein the substituent group $R^{12}$ to $R^{29}$ is selected from the group consisting of a hydroxy group, an alkoxy group, an alkyloxy carboxyl group, a cyano group and an alkyl group.

* * * * *